US008987325B2

(12) United States Patent
Sears

(10) Patent No.: US 8,987,325 B2
(45) Date of Patent: Mar. 24, 2015

(54) INHIBITORS OF ARACHIDONIC ACID FORMATION

(71) Applicant: Barry D. Sears, Danvers, MA (US)

(72) Inventor: Barry D. Sears, Danvers, MA (US)

(*) Notice: Subject to any disclaimer, the term of this patent is extended or adjusted under 35 U.S.C. 154(b) by 160 days.

(21) Appl. No.: 13/893,803

(22) Filed: May 14, 2013

(65) Prior Publication Data

US 2014/0056988 A1 Feb. 27, 2014

Related U.S. Application Data

(63) Continuation of application No. 13/315,359, filed on Dec. 9, 2011, now abandoned, which is a continuation of application No. 12/619,904, filed on Nov. 17, 2009, now abandoned, which is a continuation of application No. 12/278,226, filed as application No. PCT/US2007/003032 on Feb. 6, 2007, now abandoned.

(60) Provisional application No. 60/765,559, filed on Feb. 6, 2006.

(51) Int. Cl.
| *A61K 31/36* | (2006.01) |
| *A61P 29/00* | (2006.01) |
| *A61K 31/357* | (2006.01) |
| *A61K 31/75* | (2006.01) |
| *A61K 31/77* | (2006.01) |
| *A61K 45/06* | (2006.01) |

(52) U.S. Cl.
CPC .............. *A61K 31/357* (2013.01); *A61K 31/36* (2013.01); *A61K 31/75* (2013.01); *A61K 31/77* (2013.01); *A61K 45/06* (2013.01)
USPC ........................................................ 514/464

(58) Field of Classification Search
CPC ..... A61K 31/357; A61K 31/36; A61K 31/75; A61K 31/77; A61K 45/06
USPC .......................................... 424/526; 514/464
See application file for complete search history.

(56) References Cited

U.S. PATENT DOCUMENTS

| 5,762,935 A | 6/1998 | Forse et al. |
| 6,172,106 B1 | 1/2001 | Forse et al. |

FOREIGN PATENT DOCUMENTS

| EP | 0420327 A1 | 4/1991 |
| JP | 6-279432 | 10/1994 |
| WO | 97/25321 A2 | 7/1997 |
| WO | 99/58125 A1 | 11/1999 |
| WO | 2005/019192 A1 | 3/2005 |

OTHER PUBLICATIONS

Ambrose et al., "Toxicological Studies on Sesamol," Agricultural and Food Chemistry, 6(8):600-604, 1958.
Horig et al., "From Bench to Clinic and Back: Perspective on the 1st IQPC Translational Research Conference," Journal of Translational Medicine, 2004, 2:44, 8 pgs.

(Continued)

*Primary Examiner* — Savitha Rao
(74) *Attorney, Agent, or Firm* — K&L Gates, LLP; Christine C. Vito; Pei Wu

(57) ABSTRACT

The invention relates to a novel class of inhibitors of arachidonic acid formation that can be useful for treating inflammatory conditions. Specifically, the invention relates to derivatives of sesamol that confer lower toxicity and increased circulatory lifetimes than pure sesamol.

9 Claims, 2 Drawing Sheets

(56) References Cited

OTHER PUBLICATIONS

Hou et al., "Protective Effects of Sesamin and Sesamolin on Hypoxic Neuronal and PC12 Cells," Journal of Neuroscience Research, 74:123-133, 2003.

Inflammation document (retrieved from the Internet on May 26, 2011, URL: http://web.archive.org/web/20041126033346/ http://users.rcn.comfikimball.ma.ultranet/BiologyPages/I/Inflammation.html).

Kubota et al., "Synthesis and Pharmacological Evaluation of N-acyl-1,2,3,4-tetrahydroisoquinoline Derivatives as Novel Specific Bradycardic Agents," Bioorganic & Medicinal Chemistry, 12:871-882, 2004.

Obukowicz et al., Novel, Selective Δ6 or Δ5 Fatty Acid Desaturase Inhibitors as Antiinflammatory Agents in Mice, Journal of Pharmacology and Experimental Therapeutics, 287(1):157-166, 1998.

Schafer et al., "Failure is an Option: Learning from Unsuccessful Proof-of-Concept Trials," Drug Discovery Today, 13(21/22):913-916, 2008.

Written Opinion of the International Searching Authority for International Application No. PCT/US2007/003032, mailed on Sep. 6, 2007, 10 pgs.

INHIBITORS OF ARACHIDONIC ACID FORMATION

CROSS-REFERENCE TO RELATED APPLICATIONS

This application is a continuation of U.S. patent application Ser. No. 13/315,359, filed Dec. 9, 2011, which is a continuation of U.S. patent application Ser. No. 12/619,904, filed Nov. 17, 2009, which is a continuation of U.S. patent application Ser. No. 12/278,226, filed Aug. 4, 2008, which is the national phase of International (PCT) Patent Application Serial No. PCT/US2007/003032, filed Feb. 6, 2007, which claims priority to and the benefit of U.S. Provisional Patent Application Ser. No. 60/765,559, filed Feb. 6, 2006, the disclosures of each of which are incorporated herein by reference.

FIELD

The invention relates to compositions and methods for treating, moderating, and preventing inflammation. Specifically, the invention relates to compositions useful for inhibiting the formation of arachidonic acid, which is a precursor of pro-inflammatory eicosanoids. The invention also relates to methods of preparing and administering such compositions.

BACKGROUND

It is becoming increasingly recognized that increased inflammation is strongly associated with, if not the underlying cause of, many disease conditions including obesity, type 2 diabetes, cancer, heart disease, and neurological conditions such as multiple sclerosis and Alzheimer's disease.

It has been shown that the regulation of certain eicosanoids, a class of biologically active metabolites, can help control inflammation. While many anti-inflammatory drugs directly target the production of pro-inflammatory eicosanoids, e.g., by inhibiting the enzyme required in their production, an alternative and more sophisticated approach would be to reduce the amount of substrate upstream in the pathway, i.e., by regulating the formation of the precursors of pro-inflammatory cicosanoids, namely arachidonic acid (AA). Since AA is produced by the enzyme Δ-5-desaturase (D5D), the synthesis and/or identification of specific inhibitors of D5D can help to treat, moderate, and prevent inflammation. U.S. Pat. No. 6,172,106, the entire disclosure of which is incorporated by reference herein, has identified sesamol as a specific inhibitor of D5D. Unfortunately, sesamol is believed to be potentially toxic. Additionally, although natural compounds such as sesame lignans and curcumin have been demonstrated to exhibit inhibitory activity on D5D, their complex structures make them difficult to synthesize. Furthermore, sesame lignans also have potential toxicity. Hence, there is a need to develop non-toxic inhibitors of D5D that are easy to synthesize and can he produced on an industrial scale.

SUMMARY

It has been discovered that the toxicity of sesamol can be reduced or completely eliminated by preparing an acyl derivative of sesamol without compromising its inhibitory effect on Δ-5-desaturase (D5D).

The invention thus provides compositions comprising an acyl derivative of sesamol that are useful as anti-inflammatory agents. Specifically, the derivative is non-toxic, or has a low toxicity that can be tolerated by mammals including humans.

In some embodiments, the sesamol derivative may comprise a fatty acid. In other embodiments, the sesamol derivative may comprise a polyethylene oxide derivative. Both types of derivatives allow sesamol to be released slowly in its active form, thus reducing any potential toxicity of the composition. Such controlled release of sesamol also helps to modulate the activity of D5D in a more consistent fashion.

The compositions of the invention may be administered to human patients that require treatment for conditions associated with inflammation. Exemplary inflammation-associated conditions include, but are not limited to, obesity, type 2 diabetes, cardiovascular disease, cancer, neurological disorders, as well as any inflammatory conditions that cause pain. The compositions of the invention also may be administered to non-human mammals for veterinary purposes.

In another aspect, the invention provides methods for inhibiting the formation of arachidonic acid in a mammal by administering to the mammal a composition comprising a non-toxic chemical derivative of sesamol. The non-toxic chemical derivative may comprise an acyl derivative of sesamol. In some embodiments, the sesamol may be derivatized with at least one fatty acid. The at least one fatty acid may have a carbon chain comprising 2 to 22 carbon atoms. Additionally, the at least one fatty acid may have a degree of unsaturation in the range of 0 to 6 per fatty acid molecule. In one embodiment, the non-toxic chemical derivative is sesamol oleate. In other embodiments, the non-toxic chemical derivative may comprise a polyethylene oxide derivative. The polyethylene oxide derivative may comprise 2 to 400 repeating units.

Yet another aspect of the invention provides methods for moderating an inflammatory response in a mammal by administering to the mammal a composition comprising a non-toxic chemical derivative of sesamol. The non-toxic chemical derivative may include the embodiments described above. The composition may be administered via an enteral or parenteral route, and may comprise other biologically acceptable carriers, excipients, or diluents. Supplementary active ingredients also may be incorporated into the composition. The composition may be administered as a nutritional supplement, and may be prepared in various forms including, but not limited to, a capsule, a bar, a tablet, a powder, or a beverage package.

DETAILED DESCRIPTION OF THE INVENTION

Figure 1:
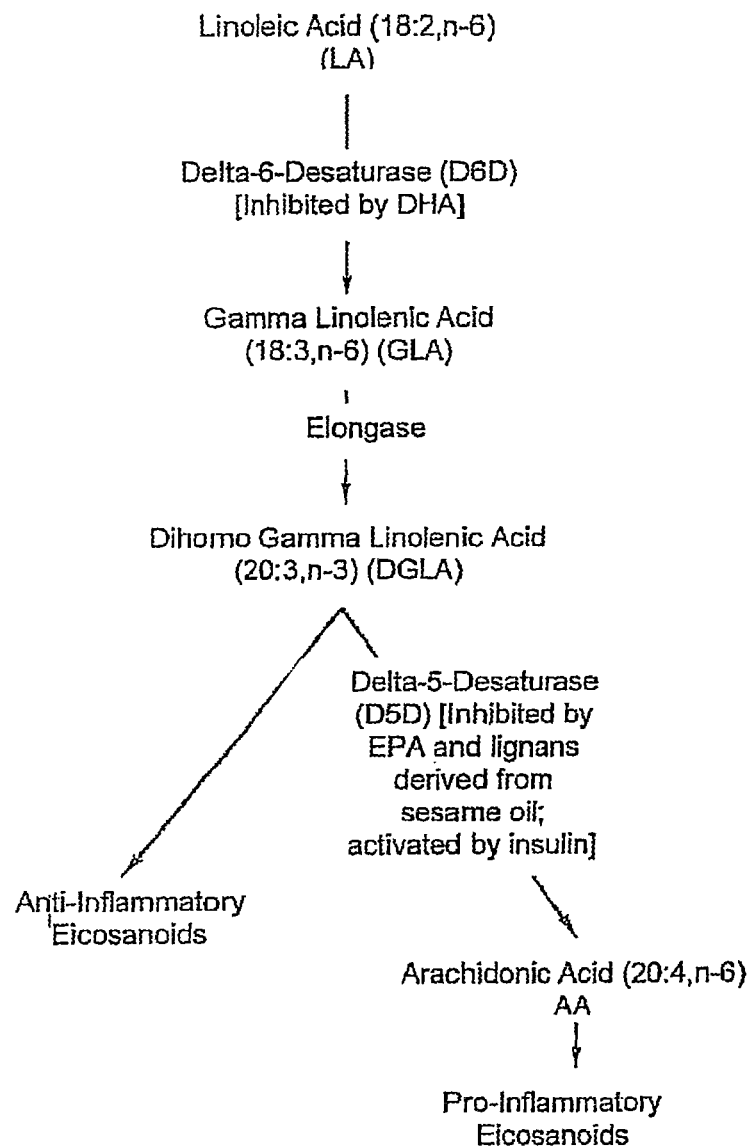
FIG. 1 illustrates the metabolic pathways leading to the production of pro-inflammatory eicosanoids.

As shown in FIG. 1, the enzyme Δ-5-desaturase (D5D) is required for converting dihomo gamma linolenic acid (DGLA) into arachidonic acid (AA). Thus, being able to control the activity of D5D via a suitable inhibitor can significantly reduce the production of AA, which in turn reduces the supply of the substrate required to generate pro-inflammatory eicosanoids.

Figure 2:
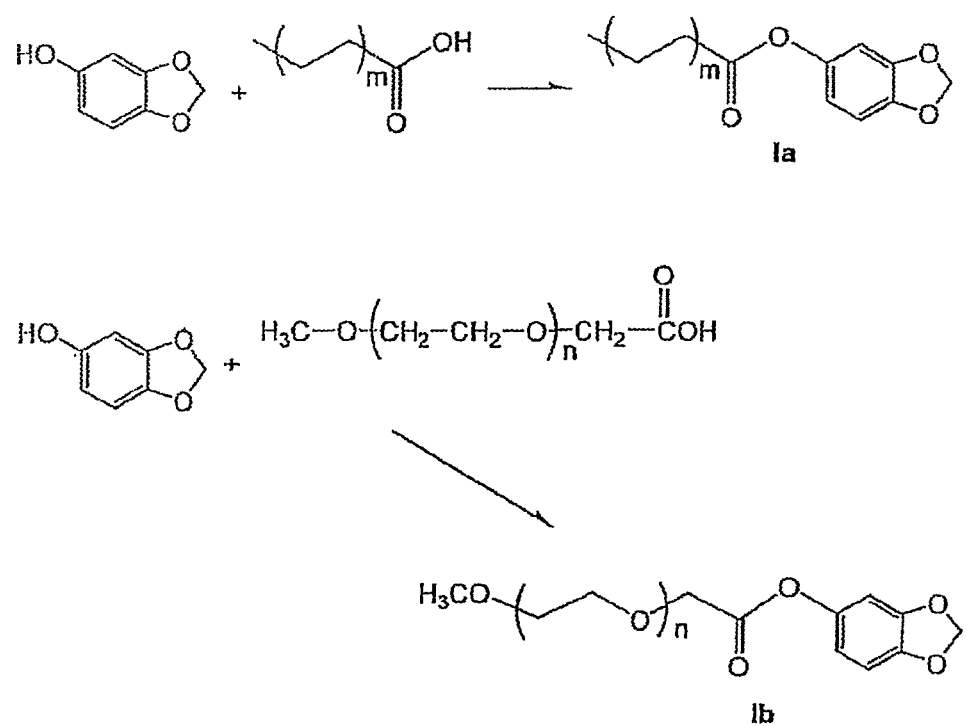
FIG. 2 shows the chemical structures of two embodiments of the invention.

Sesamol is a chemical compound that has been shown to inhibit D5D activity. However, sesamol is believed to be potentially toxic. The applicant has discovered that the toxicity of sesamol can be significantly reduced by acylating the free hydroxyl group of sesamol with a suitable carboxylic acid moiety, including fatty acids and carboxylic derivatives of polyethylene oxide. FIG. 2 shows the chemical structures of two sesamol compounds derivatized with a generic fatty acid (compound Ia) and a carboxylic acid derivative of methoxy polyethylene oxide (compound Ib), respectively. The variables m and n may be an integer in the range of 1 to 11, and 2 to 400, respectively. Such derivatization also helps to enhance the stability and bioavailability of the sesamol compound by attaching it to a biologically inert hydrophilic (i.e., polyethylene oxide) or hydrophobic (i.e., fatty acid) moiety.

Fatty acid derivatives of sesamol may be prepared from various fatty acids. Natural fatty acids, either isolated from natural sources or made synthetically, are preferred. Both saturated fatty acids and fatty acids with various degrees of unsaturation may be used, depending on the physical properties that one desires to impart to the invention. For instance, the fatty acid may have a degree of unsaturation in the range of 0 to 6 per fatty acid molecule. The fatty acid may be of various lengths and may have 2 to 22 carbon atoms per molecule. Fatty acid derivatives are hydrophobic in nature, and thus can be incorporated into circulating lipoproteins or cell membranes as a long-lived drug depot for sesamol. Examples of suitable fatty acids include, but are not limited to, palmitic acid, oleic acid, linoleic acid, alpha-linolenic acid, arachidic acid, gadoleic acid, 5,8,11,14,17-eicosapentaenoic acid, and 4,7,10,13,16,19-docosahexaenoic acid. Fatty acid derivatives of sesamol may be synthesized using standard organic chemistry via the activation of the carboxylic group with an acid chloride, an acid anhydride, or other activating agents such as 1,1 carbonyl diimidazole (CDI).

In alternative embodiments, a hydrophilic derivative of sesamol may be prepared by attaching a carboxylic acid derivative of polyethylene oxide to the sesamol molecule. As used herein, "a carboxylic acid derivative of polyethylene oxide" refers to a polymer of ethylene oxide with 2 to 400 repeating units having at least one of the two hydroxyl terminal groups converted into a carboxylic acid group. The other hydroxyl terminal group may remain underivatized or may be modified. For instance, the other terminal group may be methoxylated or converted into a second carboxylic acid group. The process of attaching one or more chains of thylene oxide to a compound is often referred to as "pegylation." In this case, the attachment of the hydrophilic polyethylene oxide moiety helps to increase the lifetime of the sesamol compound in the plasma compartment, which after the derivatization acts as a circulating depot. As the pegylated sesamol circulates in the plasma, sesamol is being slowly released into the system, which helps to reduce its toxicity.

The sesamol derivative may be delivered through traditional methods of administration such as via the enteral or various parenteral routes. For enteral administration, a composition comprising the sesamol derivative may be formulated into a pill, a soft gelatin capsule, or other methods known to those skilled in the art with or without other carriers, excipients, or diluents. Supplementary active ingredients also may be incorporated into the composition. In preferred embodiments, the composition comprising the sesamol derivative may be formulated into a soft gelatin capsule with an appropriate oil (e.g., fish oil). Parenteral administration may be through intravenous or subcutaneous injections. For a sesamol derivative comprising polyethylene oxide, the composition may be prepared as an aqueous solution, whereas if a fatty acid is used to derivatize the sesamol compound, the composition may be prepared as an emulsion, a liposome, or a micellar formation. The sesamol derivative may be delivered neat or may be combined with other pharmaceuticals or natural products (e.g., fish oil) that also have anti-inflammatory benefits.

In other embodiments, the composition of the invention may be consumed as a food product, for example, as a nutritional supplement. Preferably, the food product comprises between about 1 gram and about 60 grams of carbohydrate and between about 1 gram and about 40 grams of protein. More preferably, both protein and carbohydrate are present in the food product at a ratio of between about 0.5 and about 1.0 of protein to carbohydrate, inclusive. This ratio helps to lower secretion of insulin, thus reducing the activating impact that insulin has on D5D activity. Food products of the invention may be prepared in various forms including, but not limited to, a food bar, a confection product (e.g. an ice cream), a beverage (e.g. a ready-to-drink mix), a convenience food (e.g., a frozen meal), and a stabilized meal.

The following examples are provided to illustrate further and to facilitate the understanding of the invention and are not intended to limit the invention.

EXAMPLE 1

Acylated Sesamol Derivatives

Fatty acid is activated using a 1:1 molar amount of 1,1 carbonyl dimidazole in a dry benzene solution. The solution is taken to dryness at the completion of the activation. To the dried compound is added an equimolar amount of sesamol. The combined reactants are heated under vacuum at a low temperature for 1-2 hours. The completeness of the reaction is determined by thin layer chromatography. The acylated sesamol is then isolated by column chromatography to yield the isolated invention. The physical state of the sesamol derivative depends on the chain length of the fatty acid and its degree of unsaturation.

EXAMPLE 2

Preparation of Sesamol Oleate 17.7 mmoles of oleic acid was dissolved in 40 ml of dry benzene. To the mixture was added 17.7 mmoles of 1,1 carbonyldiimidazole. The reaction to activate the oleic acid was continued at room temperature until vigorous evolution of carbon monoxide has ceased. The reaction was then driven to completion by driving off the excess benzene under vacuum at 60° C. To the neat activated oleic acid was added 21 mmoles of sesamol. The mixture was heated at 60° C. for 2 hours under vacuum with constant rotation. The crude reaction mixture was purified using 50 grams of silica gel 60 in 2×44 cm column eluting with hexane and increasing percentages of acetone. The fractions containing the active compound were collected and evaporated to dryness giving 10 mmoles of the sesamol oleate for a 56% yield. HPLC chromatography using a 98:2 cyclohexanone/isopropyl eluting solvent give a single component with greater than 90% purity.

EXAMPLE 3

Polyethylene Oxide Sesamol Derivatives

Methoxy polyethylene oxide molecules of various chain lengths are oxidized by KMnO4 to yield a carboxylic acid derivative. The carboxylic acid derivative of methoxy polyethylene oxide is activated using a 1:1 molar amount of 1,1 carbonyl diimidazole in a dry benzene solution. The solution is taken to dryness at the completion of the activation. To the dried compound is added an equimolar amount of sesamol. The combined reactants are heated under vacuum at a low temperature for 1-2 hours. The completeness of the reaction is determined by thin layer chromatography. The acylated sesamol is then isolated by column chromatography to yield the isolated invention. The physical state of the sesamol derivative depends on the chain length of the methoxy polyethylene oxide molecule.

Variations, modifications, and other implementations of what is described herein will be occur to those of ordinary skill in the art without departing from the spirit and the essential characteristics of the invention. Accordingly, the scope of the invention is to be defined not by the preceding illustrative description but instead by the following claims, and all changes that come within the meaning and range of equivalency of the claims are intended to be embraced therein.

What is claimed is:

1. A method for reducing the level of arachidonic acid produced by $\Delta$-5-desaturase (D5D) in a mammal, the method comprising administering to a mammal a composition comprising a derivative of sesamol, wherein the derivative of sesamol is an sesamol palmitate.

2. The method of claim 1, wherein the sesamol palmitate is obtained by reacting a sesamol compound with an activated carboxylic acid.

3. The method of claim 2, wherein the activated carboxylic acid is an acid chloride, an acid anhydride, or obtained by reacting a carboxylic acid with 1,1 carbonyl diimidazole.

4. The method of claim 3, wherein the activated carboxylic acid is an activated fatty acid.

5. The method of claim 1, wherein the administering step is carried out enterally or parenterally.

6. The method of claim 1, wherein the composition is prepared as a nutritional supplement in a form selected from the group consisting of a capsule, a bar, a tablet, a powder, and a beverage package.

7. The method of claim 1, wherein the sesamol palmitate is administered to the mammal in an amount that is effective to reduce the level of arachidonic acid in the mammal.

8. The method of claim 1, wherein the composition further comprises a fish oil.

9. The method of claim 1, wherein the composition further comprises one or more proteins and one or more carbohydrates, wherein the proteins and the carbohydrates are present at a ratio of between about 0.5 and about 1.0.

* * * * *